(12) United States Patent
Bockol et al.

(10) Patent No.: US 7,658,719 B2
(45) Date of Patent: Feb. 9, 2010

(54) BANDAGE BAG

(75) Inventors: Joseph Bockol, Potomac, MD (US); Marla Anne Schram, Potomac, MD (US); John Jeffrey Rush, Potomac, MD (US)

(73) Assignee: Creative Care Medical Solutions, LLC, Potomac, MD (US)

( * ) Notice: Subject to any disclaimer, the term of this patent is extended or adjusted under 35 U.S.C. 154(b) by 255 days.

(21) Appl. No.: 11/525,593

(22) Filed: Sep. 22, 2006

(65) Prior Publication Data

US 2008/0077064 A1 Mar. 27, 2008

(51) Int. Cl.
- *A61F 5/00* (2006.01)
- *A61F 13/00* (2006.01)
- *A61M 5/32* (2006.01)
- *A61M 13/00* (2006.01)
- *A61F 5/44* (2006.01)

(52) U.S. Cl. .............. 602/3; 602/54; 602/57; 602/58; 602/63; 602/901; 206/438; 206/441; 604/179; 604/180; 604/305; 604/342; 604/336; 604/338; 604/339; 604/344; 604/345; 604/332

(58) Field of Classification Search ............ 602/3, 602/60, 54, 57, 58, 63, 901; 604/180, 337, 604/332, 342, 339, 343–344, 336, 338, 179, 604/305, 345; 128/187, 168; 206/438, 441
See application file for complete search history.

(56) References Cited

U.S. PATENT DOCUMENTS

| | | | |
|---|---|---|---|
| 2,573,791 A * | 11/1951 | Howells | 602/14 |
| 5,152,282 A * | 10/1992 | Elphick et al. | 604/180 |
| 5,605,534 A | 2/1997 | Hutchison | |
| 5,720,713 A | 2/1998 | Hutchison | |
| 5,840,675 A * | 11/1998 | Yeazell | 510/417 |
| 6,276,364 B1 | 8/2001 | Warner | |
| 2001/0018566 A1* | 8/2001 | Masini | 602/41 |
| 2003/0036715 A1* | 2/2003 | Knutson et al. | 602/43 |
| 2003/0225377 A1* | 12/2003 | Hancock et al. | 604/180 |
| 2004/0199092 A1* | 10/2004 | Biewend et al. | 602/3 |
| 2005/0211590 A1* | 9/2005 | McClure et al. | 206/438 |
| 2005/0256466 A1* | 11/2005 | Winkler | 604/337 |

OTHER PUBLICATIONS

International Search Report dated Apr. 10, 2008.

* cited by examiner

*Primary Examiner*—Patricia Bianco
*Assistant Examiner*—Tarla R Patel
(74) *Attorney, Agent, or Firm*—Fay Sharpe LLP

(57) ABSTRACT

A bandage bag provides the dual functions of holding a medical apparatus to a patient for daily wear and of serving as a waterproof bandage, especially for a catheter and its insertion site. The bandage bag comprises a bag and two adhesive layers. The bag opens along a first edge. One adhesive layer is placed along the other three edges on the anterior side of the bag. The second adhesive layer is placed along the first edge on the posterior side of the bag. The bag is attached to a patient's arm near the insertion site using the second adhesive layer. The catheter tubing and port is placed in the bag. The bag is then folded over so the first adhesive layer on the anterior side faces the arm and covers the insertion site, forming a waterproof bandage for the insertion site and the medical apparatus.

23 Claims, 7 Drawing Sheets

BANDAGE BAG

BACKGROUND

This application relates to a device for securing to a patient a medical apparatus that protrudes, in part, beyond the skin. The device carries or encloses the apparatus and also serves as a waterproof and/or protective bandage or dressing.

A central venous catheter, or vascular access device, is a long, thin, flexible tube used to deliver to a patient medications, fluids, nutrients, or other materials over a long period of time, usually several weeks or more. The catheter can be placed in a large vein near the patient's heart, such as the superior vena cava, or another large vein in the arm, neck, or chest. The catheter provides several medical advantages. It can be left in place longer than an intravenous catheter, which is located in a vein near the skin surface. It can be utilized to quickly deliver medications that affect the heart, especially if an immediate response is desired. It can also be used to measure blood pressure in the superior vena cava, which can help diagnose certain heart problems.

A peripherally inserted central catheter (PICC) is a central venous catheter which is inserted into a peripheral vein, for example in the arm of a patient, and then threaded through progressively larger veins into the superior vena cava. PICC lines are the most popular way to administer outpatient therapy by a central vein.

The handling of PICC lines in daily life can be difficult. Approximately seven inches of tubing and port will usually hang from the patient's arm and must be cared for. In addition, the catheter insertion site (where the PICC line is inserted), tubing, and port must be kept dry to prevent infection. Caring for the insertion site can be difficult. Nurses are trained to dress the insertion site with an antiseptic treatment and then place a clear protective adhesive over the area. On a periodic basis, the dressing is removed and the area is inspected, cleaned, and redressed. Removal of the adhesive can be painful. Finally, the PICC line is unsightly. Patients are discouraged from wearing long-sleeves, thus exposing a noticeable medical condition.

Some methods have been used to combat only problems of bathing. One remedy is to use a tubular sleeve and seal it at both ends, leaving the insertion site inside the sleeve. For example, U.S. Pat. No. 6,276,364 discloses a waterproof sleeve with an elastomeric band at each end to seal the sleeve. In another variation, one end of the sleeve is permanently sealed. For example, U.S. Pat. Nos. 5,605,534 and 5,720,713 each comprise a large bag which encases the entire arm and is closed off with a flexible band at the open end. Such solutions are not optimal. These remedies allow for bathing only. In the case of the large bag-type method, one hand is necessarily covered up by it, which increases the difficulty of doing many things. None of these methods allow for an elegant solution to the problem of the daily dressing of a PICC line. In addition, these remedies are cumbersome and bulky. They are not bandages in any sense; they are only water-resistant "rain coats" for the arm. They are not designed for daily wear.

There remains a need for a device which has the dual functions of holding medical apparatus (such as tubing and port) and of being able to serve as a protective bandage or dressing. Such a device should preferably restrict the patient's range of motion as little as possible, be light, and be easy to apply by oneself.

BRIEF DESCRIPTION

Disclosed herein, in various embodiments, are bandage bags which have a dual function of holding or enclosing a medical apparatus protruding beyond the skin (i.e. tubing, ports, catheters, etc.) and serving as a bandage or dressing for daily wear.

In one embodiment, the bandage bag comprises a rectangular or square enclosure or receptacle bag and two adhesive layers. The bag is open along a superior edge for placing medical apparatus therein. The first adhesive layer is placed on the anterior side of the bag along three edges: a first lateral edge, an inferior edge, and a second lateral edge. The second adhesive layer is placed on the posterior face of the bag along the superior edge.

In additional embodiments, the bandage bag further comprises at least one wing which is located on the posterior face along the superior edge and is attached to a lateral edge such that the wing can be pivoted to extend laterally from the bag or to cover at least a portion of the second adhesive layer. In more specific embodiments, the at least one wing has a first side which contacts at least a portion of the second adhesive layer and has a third adhesive layer disposed on the first side.

In further embodiments, the bandage bag has a total of two wings. One wing is attached to the first lateral edge and the other wing is attached to the second lateral edge.

In still further embodiments, the bandage bag further comprises a removable backing or release layer shaped to cover the first adhesive layer.

In other embodiments, further materials may be disposed on the anterior face of the bandage bag. These materials aid in treating and dressing the catheter insertion site.

In still additional embodiments, alternative configurations, such as triangular, circular, elliptical, and other suitable shapes, can be utilized. The bandage bag may also be sized or shaped to meet or conform to the patient's specific body configurations. In such configurations, the adhesive layer(s) are preferably placed on the outer or peripheral edges of the bandage bag.

Methods for using the bandage bag to contain medical apparatus and to form a protective and/or waterproof bandage or dressing over a catheter insertion site are also provided. The bandage bag is attached near the catheter insertion site with the second adhesive layer. Medical apparatus are placed inside the bag. The bag is then folded across a horizontal axis such that the catheter insertion site is covered by the anterior face of the bandage bag. The protective and/or waterproof bandage is then formed by attaching the bandage bag with the first adhesive layer such that it surrounds the insertion site.

These and other non-limiting features or characteristics of the present disclosure will be further described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
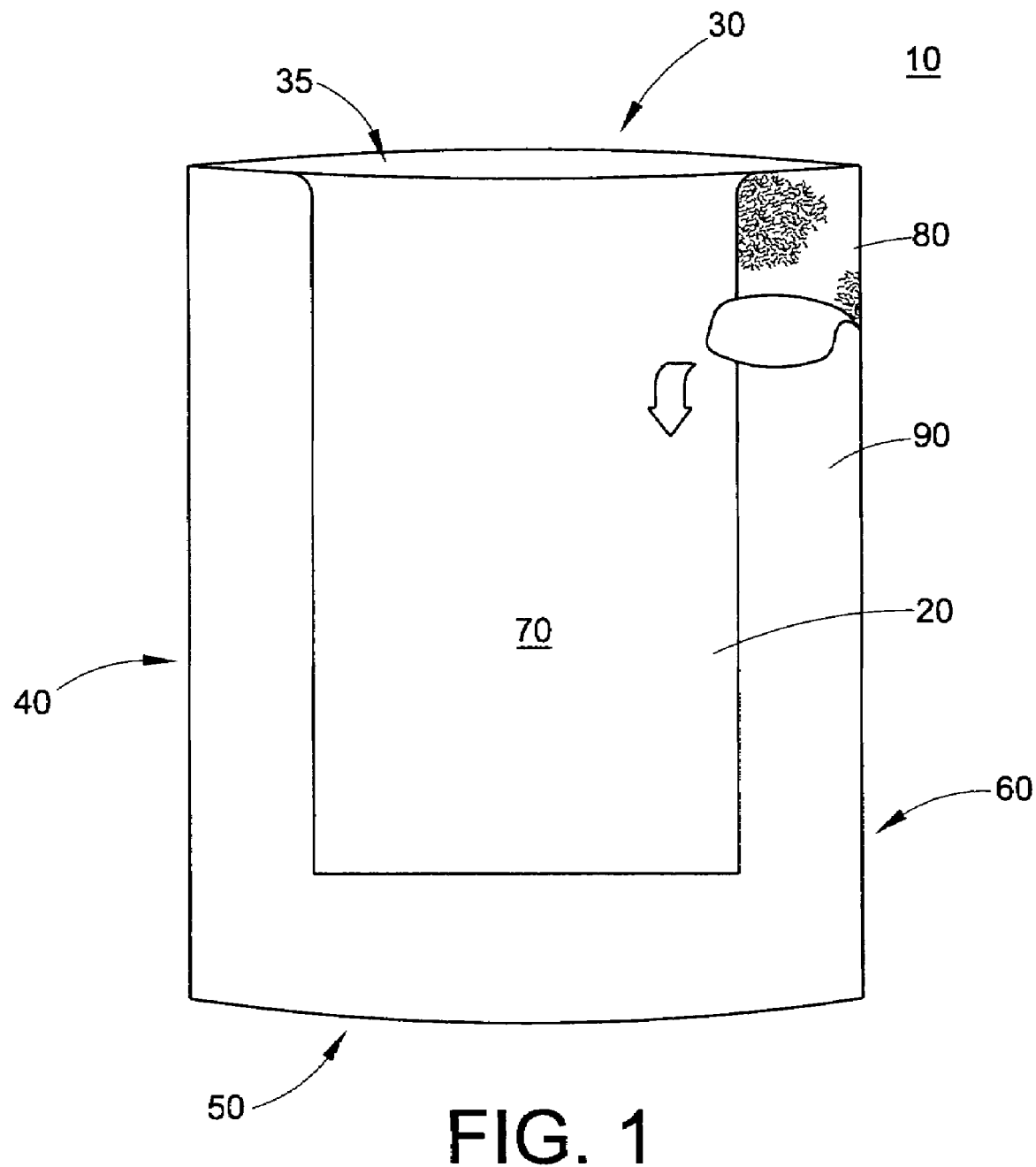
FIG. 1 is an anterior view of an exemplary embodiment of the bandage bag.

The exemplary embodiments of this application are more particularly described below with reference to the drawings. Although specific terms are used in the following description for clarity, these terms are intended to refer only to the particular structure of the various embodiments selected for illustration in the drawings and not to define or limit the scope of the application. The same reference numerals are used to identify the same structure in different Figures. The structures in the Figures are not drawn according to their relative proportions and the drawings should not be interpreted as limiting the application in size, relative size, or location.

FIG. 1 is an anterior, or front, view of an exemplary embodiment of the bandage bag. The bandage bag 10 comprises an enclosure bag 20. The enclosure bag 20 is open along a superior edge 30 and can be accessed through an opening 35 to place items, such as medical apparatus, inside the enclosure bag 20. The enclosure bag 20 has a first lateral edge 40, an inferior edge 50, and a second lateral edge 60. The anterior face 70 of the enclosure bag 20 is visible. A first adhesive layer 80 is disposed along the first lateral edge 40, inferior edge 50, and second lateral edge 60. Note that the adhesive 80 does not completely cover the anterior face 70, but only its edges. A removable backing 90 is shaped to cover the first adhesive layer 80 for ease and convenience in handling. The backing 90 is removed when the bandage bag 10 is used.

Figure 2:
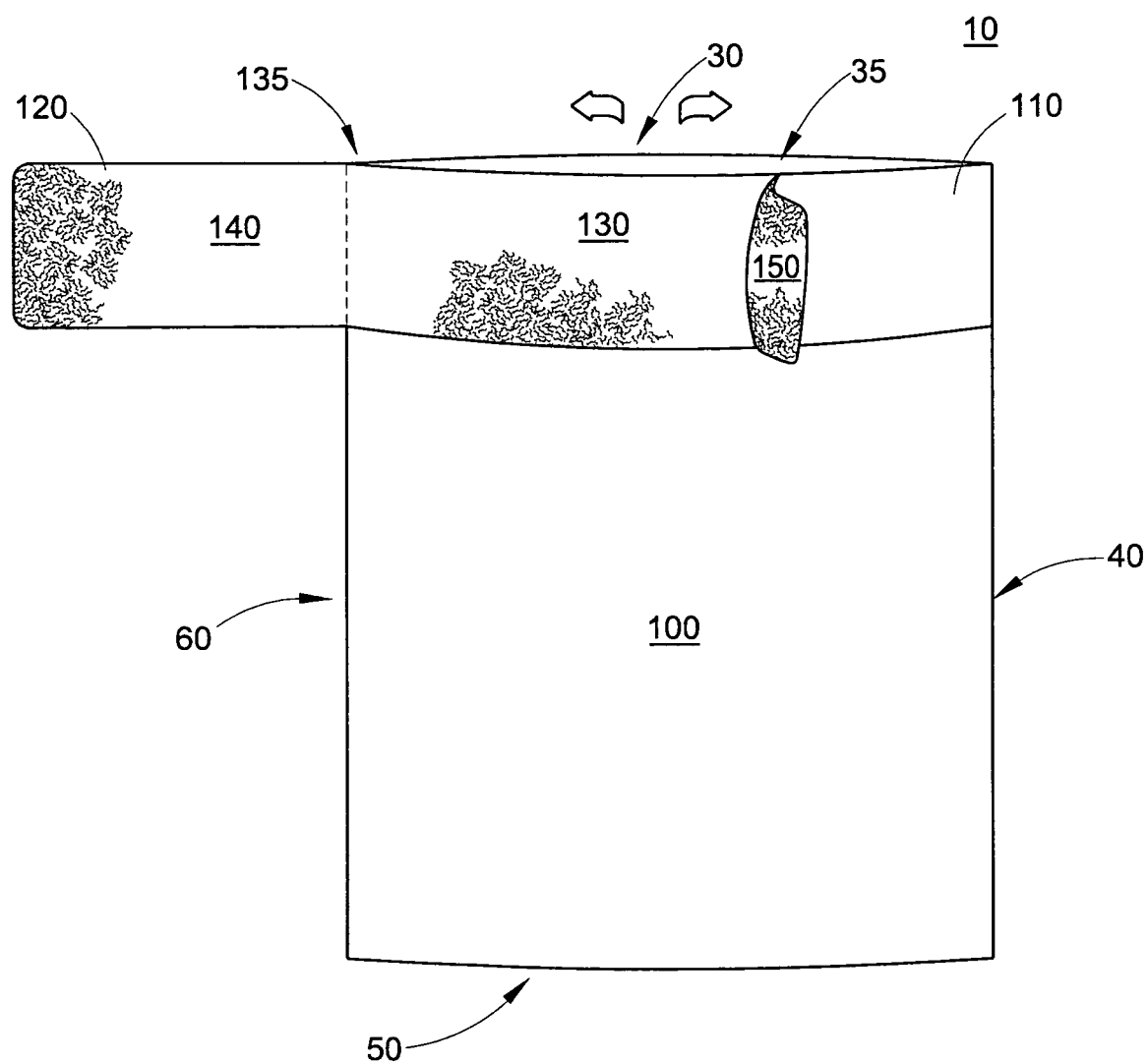
FIG. 2 is a posterior view of an exemplary embodiment of the bandage bag wherein the bandage bag has two wings.

FIG. 2 is a posterior, or back, view of an exemplary embodiment of the bandage bag. A second adhesive layer 130 is disposed along the superior edge of the posterior face 100. Again, note the posterior face 100 is not completely covered by the adhesive layer 130. In the depicted embodiment, the bandage bag 10 has two wings: a first wing 110 and a second wing 120. The wings are located on the posterior face 100 along the superior edge 30. Each wing is attached to a lateral edge such that the wing can be pivoted to extend laterally from the enclosure bag 20. For example, the second wing 120 is attached to the second lateral edge 60 at the attachment point 135 and extends laterally. A third adhesive layer 140 is disposed upon the second wing 120. The first wing 110 is shown covering approximately one-half of the second adhesive layer 130. Part of the third adhesive layer 150 on the first wing 110 is visible. The wings are both extended laterally, from the enclosure bag 20, and since they each have a third adhesive layer, can be secured to the arm.

Figure 3:
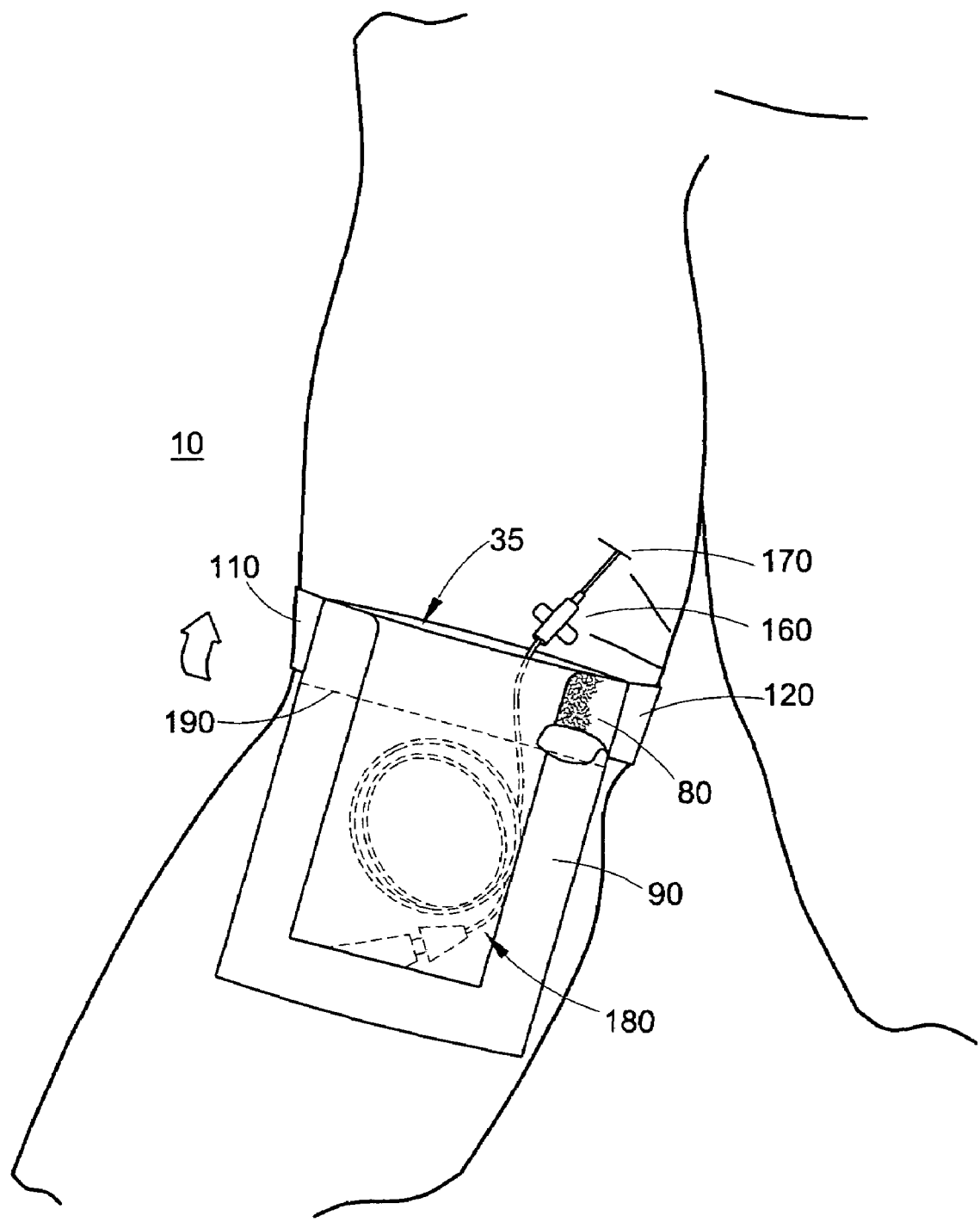
FIG. 3 is a diagram showing one use of the bandage bag.

FIG. 3 is a diagram showing one use of the bandage bag. The diagram depicts the arm of a patient with a PICC inserted. The catheter 160 and the catheter insertion site 170 are visible on the arm. The anterior face of the bandage bag 10, with the first adhesive layer 80 and the removable backing 90, is also visible. Here, the bandage bag 10 is placed above the antecubital fossa (the fold of the elbow) and near the catheter insertion site 170. The two wings 110 and 120 have been extended laterally to expose the second adhesive layer and the third adhesive layer of each wing; these adhesive layers attach the bandage bag to the arm of the patient. The medical apparatus 180 (tubing and port in this diagram) have been inserted into the bandage bag 10 through the bag opening 35. The bandage bag is then folded across a horizontal axis 190 such that the catheter insertion site is covered by the anterior face of the bandage bag and the first adhesive layer 80 faces the arm. A waterproof bandage or dressing is formed by attaching the bandage bag 10 to the arm with the first adhesive layer 80. A pocket will be formed on three sides by the first adhesive layer 80 and on the fourth side by the fold along the horizontal axis 190. The catheter insertion site 170 is located within the pocket created by the fold. Note that the horizontal axis 190 may be located almost anywhere along the length of the bandage bag as long as the bag opening 35 is closed after the bandage bag has been folded. In practice, however, the horizontal axis 190 will generally be near the superior edge of the bandage bag.

Figure 4:
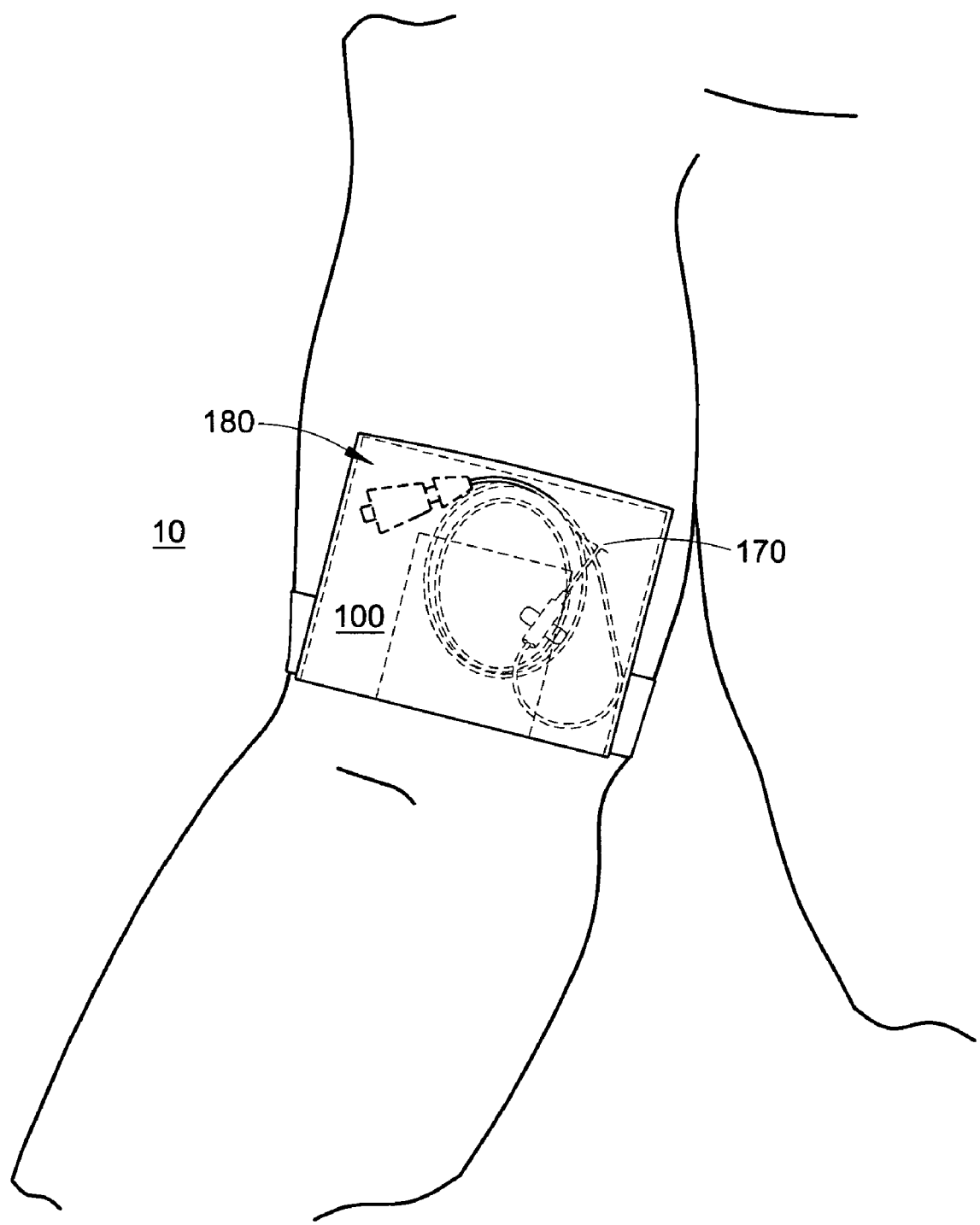
FIG. 4 is a diagram showing the bandage bag when folded over as a waterproof bandage.

FIG. 4 shows the bandage bag after it has been folded over as a waterproof bandage. The posterior face 100 of the bandage bag 10 is now visible. The medical apparatus 180 and the catheter insertion site 170 are now segregated from the outside environment by the water-resistant seal. In particular, the catheter insertion site 170 is protected from moisture and other dirt or debris. This decreases the chance of infection, promoting faster healing and patient well-being. It also allows the patient to bathe and shower without hassle or worry. The bandage bag allows the tubing and port to be contained securely, eliminating the need for daily maintenance. The waterproof bandage is also easier to apply and covers a smaller portion of the arm than other larger non-bandage devices that are solely intended for use while bathing. Note that the elbow in particular is not covered, allowing the patient to have full range of motion. The insertion site is discreetly covered, so others cannot see the wound. The bandage bag is also thin and light, which allows the wearing of long-sleeve clothing.

Figure 5:
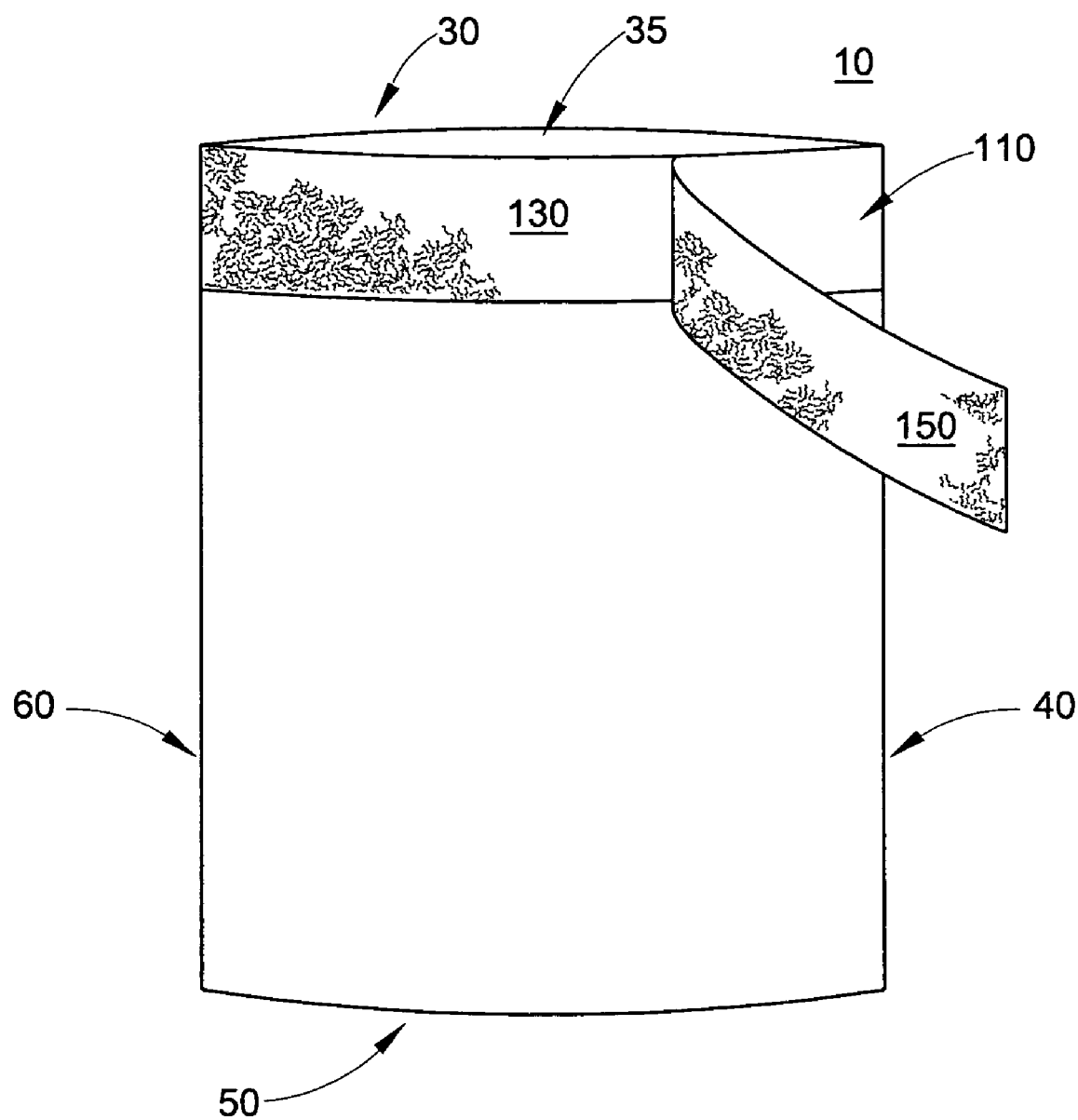
FIG. 5 is a posterior view of an exemplary embodiment of the bandage bag wherein the bandage bag has one wing.

FIG. 5 is a posterior view of another exemplary embodiment of the bandage bag. This embodiment differs from that depicted in FIG. 2 in that the bandage bag 10 has only one wing 110. The wing 110 entirely covers the second adhesive layer 130 when folded against the superior edge 30 of the bandage bag. Here, the wing 110 is again attached to the first lateral edge 40. A third adhesive layer 150 is disposed on one side of the wing 110.

The enclosure bag portion 20 of the bandage bag can be made from a flexible, waterproof material. Such materials may include cellophane-like materials, including, but not limited to, plastic, polymer, latex, or rubber. It may have any dimensions desired. In specific embodiments, the bag is square or rectangular (prior to being folded). In one specific embodiment, the bag has dimensions of about 8 cm in length and about 8 cm in width. The bag opening 35 generally runs along the entirety of the superior edge 30. However, this is not required and the opening may be less than the entirety of the superior edge. For example, the bag opening may run only within the middle of the superior edge so that the superior edge is sealed at its ends (near the lateral edges) in some embodiments. When the bandage bag is folded over, the opening 35 will then be wholly contained within the waterproof pocket.

Figure 6:
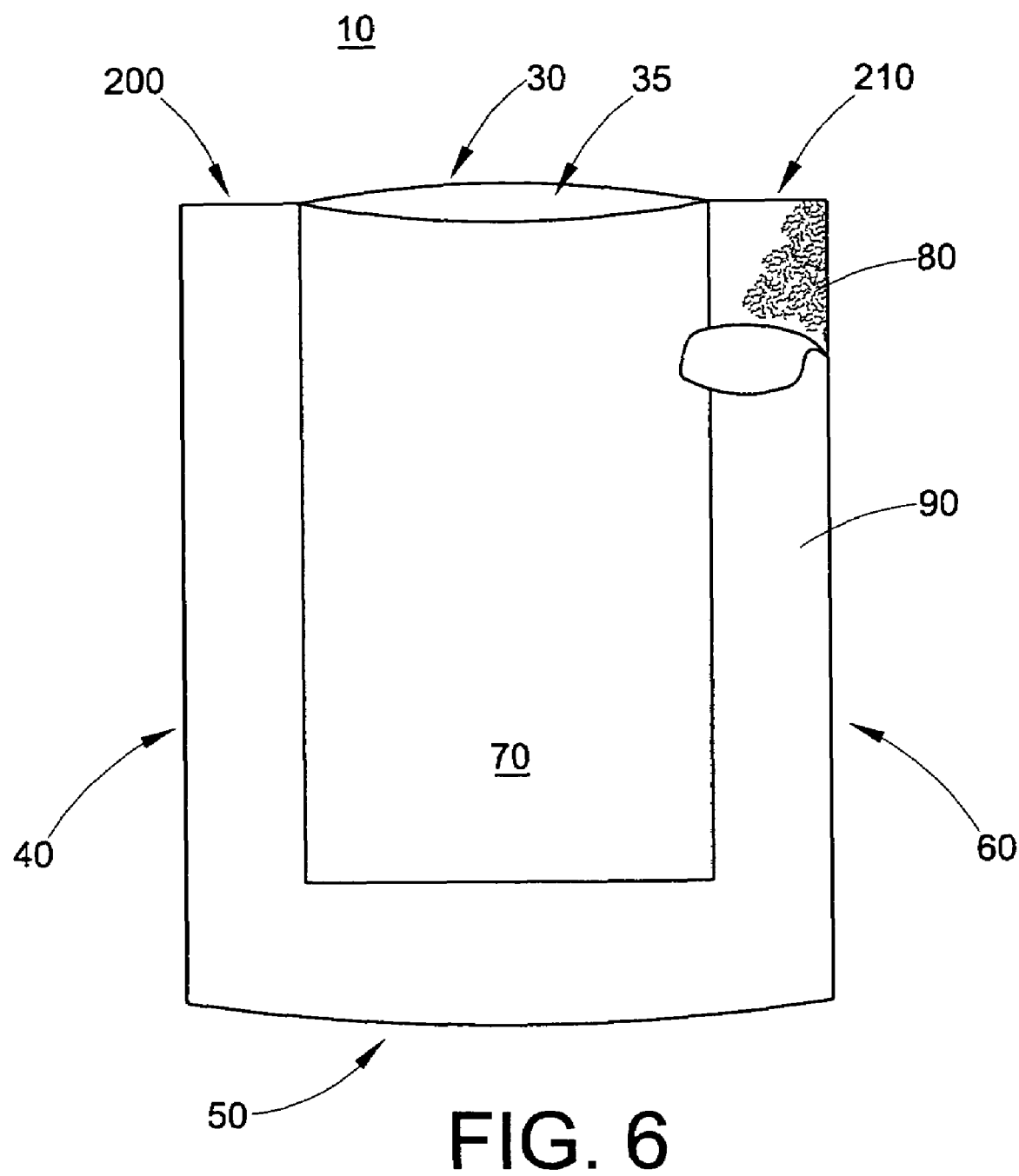
FIG. 6 is an anterior view of an exemplary embodiment of the bandage bag wherein the opening of the bandage bag is sealed on the ends of the superior edge.

FIG. 6 shows such an embodiment. In this anterior view of the bandage bag 10, the bag opening 35 does not constitute the entirety of the superior edge. Instead, the superior edge is sealed at a first superior end 200 and a second superior end 210. Each superior end adjoins a lateral edge 40 or 60. The bag opening 35 runs only within the middle of the superior edge, from the first superior end 200 to the second superior end 210.

Generally, the adhesive used in the first, second, and third adhesive layers should be a medical-grade adhesive. The adhesive should also be water-resistant and non-irritating to the skin.

In embodiments where the bandage bag does not have wings, a removable backing is provided to cover both the first and second adhesive layers. In exemplary embodiments, however, the bandage bag has at least one wing. The at least one wing is located on the posterior face along the superior edge and is attached to a lateral edge such that the wing can be pivoted to extend laterally from the bag or to cover at least a portion of the second adhesive layer. In the preferred embodiment, the bandage bag has a total of two wings, wherein one wing is attached to the first lateral edge and the other wing is attached to the second lateral edge.

As can be seen in FIG. 1, the first adhesive layer 80 does not cover the whole of the anterior face 70. If desired, other materials can be disposed on the anterior face of the bandage bag. Such materials would, once the bandage bag has been folded, be contained within the pocket containing the catheter insertion site 170. For example, a water absorbent material could be placed there to soak up any moisture which might form inside the waterproof seal (for example, from condensation or sweat). Similarly, an antibiotic and/or antifungal impregnated material could be placed there to prevent any bacterial or fungal growth in or around the catheter insertion site.

Figure 7:
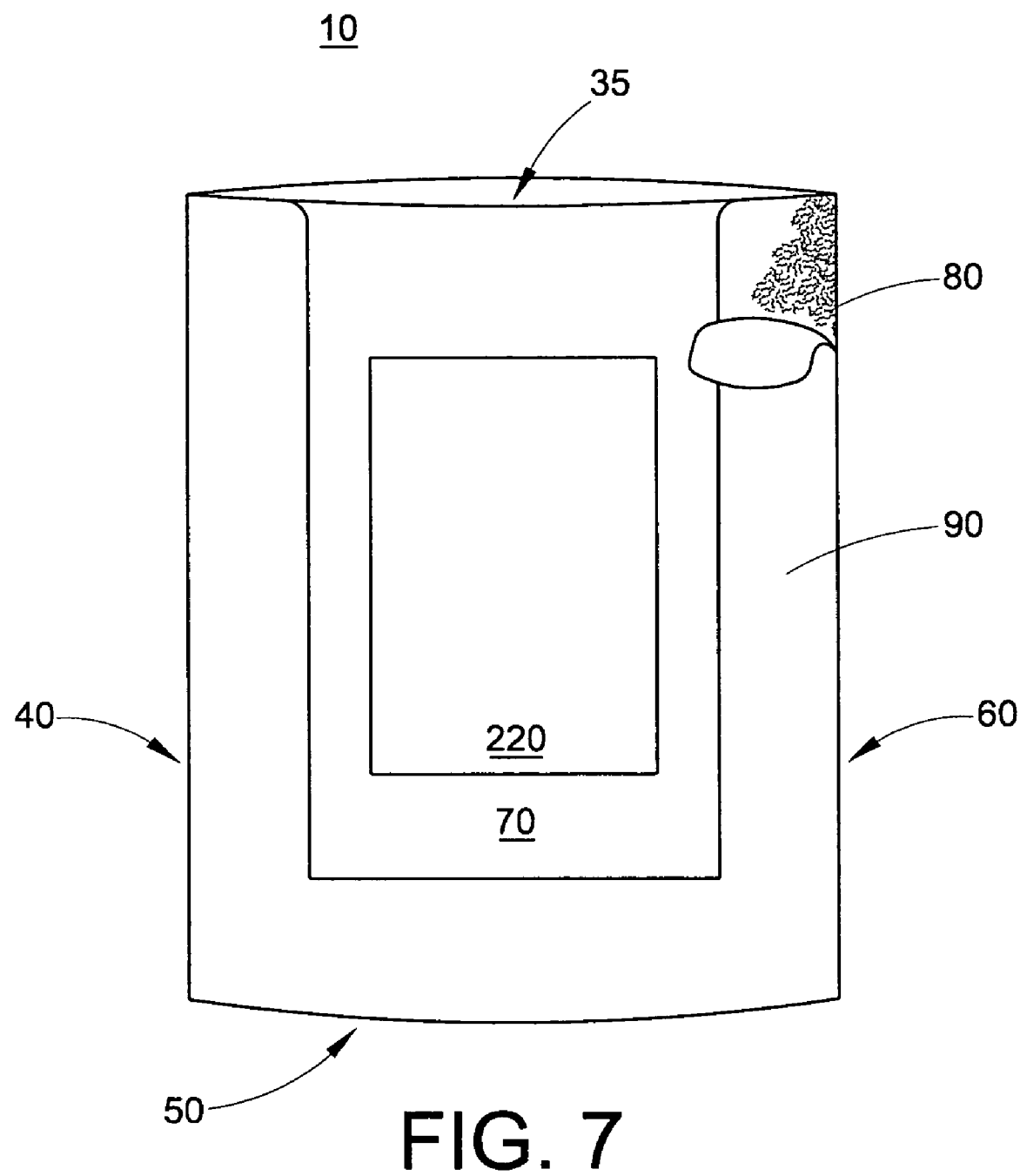
FIG. 7 is an anterior view of an exemplary embodiment of the bandage bag wherein an impregnated material is present on the anterior face of the bandage bag.

FIG. 7 is an anterior view of such an exemplary embodiment. Here, a material pad 220 is present on the anterior face 70 of the bandage bag 10. This pad could be impregnated with an antibiotic and/or antifungal. It could also be water-absorbent. Although a material pad is depicted, a pad is not required to place such materials on the anterior face and is simply used here for clarity. Antibiotic or antifungal could be applied to the anterior face in a cream or paste, for example.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A bandage bag, comprising:
   a bag having an opening along a superior edge;
   a first adhesive layer disposed on an exterior anterior face of the bag along a first lateral edge, an inferior edge, and a second lateral edge of the bag; and
   a second adhesive layer disposed on an exterior posterior face of the bag along the superior edge of the bag, the second adhesive layer being useful for attaching the bag to a patient.

2. The bandage bag of claim 1, further comprising at least one wing which is located on the exterior posterior face along the superior edge and is attached to a lateral edge such that the wing can be pivoted to extend laterally from the bag.

3. The bandage bag of claim 2, wherein the at least one wing has a first side and a second side, the first side can contact at least a portion of the second adhesive layer; and a third adhesive layer is disposed on the first side.

4. The bandage bag of claim 2, wherein the bandage bag has a total of two wings, wherein one wing is attached to the first lateral edge and the other wing is attached to the second lateral edge.

5. The bandage bag of claim 1, further comprising a removable backing shaped to cover the first adhesive layer.

6. The bandage bag of claim 1, wherein the opening runs only within the middle of the superior edge.

7. The bandage bag of claim 1, wherein the bag is made of a waterproof material.

8. The bandage bag of claim 1, wherein the bag is made of cellophane-like materials.

9. The bandage bag of claim 1, wherein the bag is made of plastic, polymer, latex, or rubber.

10. The bandage bag of claim 1, wherein the bag is square or rectangular.

11. The bandage bag of claim 1, wherein the bag has dimensions of about 8 cm by about 8 cm.

12. The bandage bag of claim 1, further comprising a water absorbent material disposed on the exterior anterior face.

13. The bandage bag of claim 1, further comprising an antibiotic impregnated material disposed on the exterior anterior face.

14. The bandage bag of claim 1, further comprising an antifungal impregnated material disposed on the exterior anterior face.

15. A method of using a bandage bag to contain associated medical apparatus and to form a waterproof bandage over an associated catheter insertion site on an associated arm, comprising:
   providing a bandage bag comprising:
      a bag having an opening along a superior edge;
      a first adhesive layer disposed on an exterior anterior face of the bag along a first lateral edge, an inferior edge, and a second lateral edge of the bag; and
      a second adhesive layer disposed on an exterior posterior face of the bag along the superior edge of the bag;
   attaching the bandage bag near the associated catheter insertion site with the second adhesive layer to the associated arm;
   containing the associated medical apparatus inside the bag;
   folding the bag across a horizontal axis such that the associated catheter insertion site is covered by the exterior anterior face of the bandage bag; and
   forming a waterproof bandage by attaching the bandage bag with the first adhesive layer to the associated arm.

16. The method of claim 15, wherein the bandage bag further comprises at least one wing which is located on the exterior posterior face along the superior edge and is attached to a lateral edge such that the wing can be pivoted to extend laterally from the bag or to cover at least a portion of the second adhesive layer; and further comprising the step of:
   extending the at least one wing laterally to expose the second adhesive layer.

17. The method of claim 15, wherein the bandage bag further comprises two wings located on the exterior posterior face along the superior edge, wherein one wing is attached to the first lateral edge and the other wing is attached to the second lateral edge and each wing can be pivoted to extend laterally from the bag; and further comprising the step of:
   extending each wing laterally to expose the second adhesive layer.

18. A bandage bag, comprising:
   a bag having an opening along a superior edge;
   a first adhesive layer disposed on an exterior anterior face of the bag along a first lateral edge, an inferior edge, and a second lateral edge of the bag;

a second adhesive layer disposed on an exterior posterior face of the bag along the superior edge of the bag; and two wings, wherein each wing is located on the exterior posterior face along the superior edge and has a third adhesive layer disposed on one side of the wing;

wherein one wing is attached to the first lateral edge and the other wing is attached to the second lateral edge such that each wing can be pivoted to extend laterally from the bag or to cover at least a portion of the second adhesive layer, the second adhesive layer being useful for attaching the bag to a patient.

19. The bandage bag of claim 18, wherein the opening runs only within the middle of the superior edge.

20. The bandage bag of claim 18, further comprising a material disposed on the exterior anterior face which is water-absorbent, impregnated with an antibiotic, or impregnated with an antifungal.

21. A bandage bag, comprising:

a bag having an opening along a superior edge;

a first adhesive layer disposed on an exterior anterior face of the bag along a first lateral edge, an inferior edge, and a second lateral edge of the bag, but not the superior edge of the bag; and a second adhesive layer disposed on an exterior posterior face of the bag along the superior edge of the bag, the second adhesive layer being useful for attaching the bag to a patient.

22. The bandage bag of claim 21, further comprising at least one wing which is located on the exterior posterior face along the superior edge and is attached to a lateral edge such that the wing can be pivoted to extend laterally from the bag;

wherein the at least one wing has a first side and a second side, the first side can contact at least a portion of the second adhesive layer; and a third adhesive layer is disposed on the first side so that when the wing is extended laterally from the bag, the third adhesive layer and the second adhesive layer face in the same direction.

23. A bandage bag, comprising:

a bag having an exterior anterior face, an exterior posterior face, and an opening along a superior edge;

a first adhesive layer disposed on the exterior anterior face along a first lateral edge, an inferior edge, and a second lateral edge of the bag;

a second adhesive layer disposed on the exterior posterior face along the superior edge of the bag, the second adhesive layer being useful for attaching the bag to a patient.

* * * * *